United States Patent
Breitenbach et al.

(10) Patent No.: US 6,599,931 B1
(45) Date of Patent: Jul. 29, 2003

(54) TEST SYSTEM FOR CHARACTERIZING THE COMPATIBILITY OF BIOACTIVE SUBSTANCES AND POLYVINYLPYRROLIDONE

(75) Inventors: Jörg Breitenbach, Mannheim (DE); Robert Heger, Heidelberg (DE); Dirk Simon, Mutterstadt (DE); Bernd Liepold, Mannheim (DE)

(73) Assignee: Abbott GmbH & Co. KG, Ludwigshafen (DE)

( * ) Notice: Subject to any disclaimer, the term of this patent is extended or adjusted under 35 U.S.C. 154(b) by 0 days.

(21) Appl. No.: 09/396,363

(22) Filed: Sep. 18, 1999

(30) Foreign Application Priority Data

Sep. 18, 1998 (DE) .......................................... 198 42 914

(51) Int. Cl.[7] ..................... A01N 43/36; A61K 31/4015
(52) U.S. Cl. ..................... 514/424; 514/423; 514/408; 424/405; 424/464; 424/465; 424/469; 424/470; 424/484; 424/486; 424/487
(58) Field of Search ................... 424/464, 465, 424/469, 470, 484, 486, 489, 405; 514/408, 423, 424; 548/400, 531–536

(56) References Cited

U.S. PATENT DOCUMENTS

| | | | | |
|---|---|---|---|---|
| 3,772,186 A | * | 11/1973 | Hort | ........................... 208/326 |
| 3,872,100 A | * | 3/1975 | Hort | ...................... 260/326.25 |
| 4,801,460 A | | 1/1989 | Goertz et al. | ................ 424/465 |
| 5,405,616 A | * | 4/1995 | Wunderlich et al. | ........ 424/451 |
| 5,456,923 A | * | 10/1995 | Nakamichi et al. | ......... 424/489 |
| 5,716,642 A | * | 2/1998 | Bagchi et al. | ............... 424/489 |

FOREIGN PATENT DOCUMENTS

| | | |
|---|---|---|
| DE | 19641437 | 4/1998 |
| EP | 240904 | 10/1987 |
| WO | 9815291 | * 4/1998 |

OTHER PUBLICATIONS

Chiou et al., *J. of Pharm. Sci.*, vol. 60, No. 9, 1971, 1281–1302.

* cited by examiner

*Primary Examiner*—Russell Travers
*Assistant Examiner*—Shahnam Sharareh
(74) *Attorney, Agent, or Firm*—Keil & Weinkauf

(57) ABSTRACT

A test system for characterizing the compatibility of bioactive substances with polyvinylpyrrolidones in a solid dispersion consisting of one or more bioactive substances and 1,3-bis(1-pyrrolidonyl)butane.

5 Claims, No Drawings

TEST SYSTEM FOR CHARACTERIZING THE COMPATIBILITY OF BIOACTIVE SUBSTANCES AND POLYVINYLPYRROLIDONE

The present invention relates to a test system for characterizing the compatibility of bioactive substances with polyvinylpyrrolidones in a solid dispersion consisting of one or more bioactive substances and 1,3-bis(1-pyrrolidonyl) butane. The invention further relates to a method for characterizing the compatibility and to the use of 1,3-bis(1-pyrrolidonyl)butane as solvent in a test system of this type.

Solid dispersions, that is to say homogeneous extremely fine disperse phases of two or more solids, and the special case thereof called "solid solutions" (molecularly disperse systems) and their use in pharmaceutical technology are generally known (cf. Chiou and Riegelman, J. Pharm. Sci., 60, 1281–1300 (1971)).

Solid solutions can be produced by melting processes or by the solution process.

A particularly suitable polymeric auxiliary for producing such solid dispersions or solid solutions is polyvinylpyrrolidone (PVP). PVP-based solid solutions of bioactive substances can be produced particularly advantageously by melt extrusion as described, for example, in EP-A 240904.

However, there are minimum requirements on the amounts employed to produce melt extrudates. If only relatively small amounts of active ingredient are available, it cannot be predicted with certainty whether an active ingredient will form solid solutions with PVP whether in the melt or in coprecipitates. However, it is precisely when drug products based on new active ingredients are being developed that only relatively small amounts of the active ingredient are frequently available so that the possibility of prediction with the aid of a simple test system appears to be extremely desirable.

It is likewise desirable to be able to make predictions concerning the stability of solid solutions or solid dispersions. This is because, depending on the compatibility of active ingredient and PVP, the previously homogeneous disperse phase may become inhomogeneous, or the active ingredient may recrystallize. Such phase separation or recrystallization is, of course, unwanted because of the change in the homogeneity and the release characteristics associated therewith.

It is an object of the present invention find a test system which makes it possible in a simple manner to characterize the compatibility of bioactive substances and PVP in a solid dispersion.

We have found that this object is achieved by the test system defined at the outset. We have also found a method for characterizing the compatibility of bioactive substances with polyvinylpyrrolidones in a solid dispersion, which comprises dispersing or dissolving the bioactive substance in 1,3-bis(1-pyrrolidonyl)butane, and assessing the resulting dispersion or solution spectroscopically.

The test system according to the invention consists, on the one hand, of one or more bioactive substances and, on the other hand, of 1,3-bis(1-pyrrolidonyl)butane as solvent or dispersant.

The preparation of 1,3-bis(1-pyrrolidonyl)butane is known per se. Thus, for example, Breitenbach et al., Naturwissenschaften 42, 1955, 155;440, describe the dimerization of N-vinylpyrrolidone under acidic reaction conditions and subsequent hydrogenation of the resulting 1,3-bis(1-pyrrolidonyl)-1-butene to 1,3-bis(1-pyrrolidonyl)butane. 1,3-Bis(1-pyrrolidonyl)butane is a colorless oily liquid with a boiling point of 205–215° C. (0.2 mbar). DE-A 196 41 437 discloses that 1,3-bis(1-pyrrolidonyl)butane (also called DHVP hereinafter) is suitable as solvent or solubilizer for cosmetic or pharmaceutical active ingredients.

The test system is suitable in principle for all pharmaceutical active ingredients, crop protection agents, food supplements or cosmetic active ingredients. It is also possible to examine the compatibility of detergent enzymes or dyes with PVP. The miscibility of non-bioactive formulation aids such as sugars, sugar alcohols or other polymeric aids can also be examined. Suitable polyvinylpyrrolidones (PVP) are all types of PVP with Fikentscher K values of from 10 to 110.

Compatibility means for the purpose of this invention the tendency of a substance to form a stable homogeneous solid dispersion with PVP, this solid dispersion being, in particular, a solid solution, that is to say a molecular dispersion of the components in one another.

To carry out the method according to the invention, a solution or dispersion of the active ingredient or mixtures of active ingredients in DHVP is prepared. The ratios of the amounts can in principle be chosen without restriction and naturally depend essentially on the properties of the active ingredient. However, it is advisable to choose the concentration ranges in the test system so that they correspond to active ingredient contents typical of extruded forms, that is to say generally from 0.1 to 70, preferably 10 to 30% by weight of active ingredient, based on the total weight of the test system. However, it is also possible in the individual case to prepare solutions or dispersions with a concentration of 60% by weight or even higher. It is preferred to carry out test series with increasing active ingredient contents. The active ingredient(s) are weighed out, mixed with the appropriate amounts of DHVP and preferably stirred, normally with a typical laboratory magnetic stirrer at 5 to 200 rpm. If a substance does not dissolve at room temperature, the test system can also be heated. The heating is preferably carried out so as to correspond approximately to the heating rate in a subsequent melt formulation, that is to say at 0.5 to 5° C./min. The test system is preferably heated to a maximum of 140° C. However, it is also possible in the individual case to heat to the boiling point of DHVP. The test system is then allowed to cool to room temperature.

The prepared test systems are assessed spectroscopically. This preferably takes place visually using a microscope, for example using a conventional laboratory microscope with a resolution of 0.04 N.A. It is found in this way whether clear solutions or dispersions form. The recrystallization behavior is also assessed. The recrystallization behavior immediately after cooling to room temperature is an important criterion especially for test systems in which the active ingredient has been induced to dissolve by heating. Test systems in which the active ingredient does not recrystallize immediately after stopping the stirring or after cooling are investigated for long-term stability:

leaving to stand at room temperature for 24 hours
after storage for 1 month, 3 months, 6 months in climate zone 2 (25° C., 60% relative humidity) and climate zone 4 (20° C., 70% relative humidity)
stress storage at 40° C., 75% relative humidity for up to 6 months.

Investigation is always of whether the active ingredient has recrystallized out of the solution.

It is also possible to examine the test systems for their amorphous nature with the aid of confocal Raman spectroscopy.

The method of differential scanning calorimetry is likewise suitable.

It has emerged that conclusions can be drawn directly from the recrystallization behavior from a DHVP solution about the stability of a solid solution of an active ingredient with polyvinylpyrrolidones obtained by melt extrusion or by coprecipitation. There is a good correlation between the stability of a solution of the active ingredient in DHVP and the stability of an active ingredient-containing PVP melt extrudate or coprecipitate. It is also possible from the dissolving behavior of the active ingredient in DHVP to draw conclusions directly about the tendency of a substance to form solid solutions with PVP, specifically in relation both to a suitable temperature profile for melt processes such as extrusion and to the amount of active ingredient which can be incorporated.

This means that the test system makes it possible to predict in a straightforward manner the compatibility of bioactive substances with polyvinylpyrrolidones, in particular of products obtainable by melt processes.

There has been investigation of, for example, the dissolving behavior of acetylcysteine, acetylsalicylic acid, anipamil HCl, bentazone, benzocaine, bezafibrate, biperiden, Butazolidin, captopril, carbamazepine, chloramphenicol, cromoglicic acid, clotrimazole, caffeine, cyclosporin, diazepam, diclofenac sodium, dilliazon, diltiazem, dimetridazole, diphenhydramine HCl, 5,5-diphenylhydantoin, erythromycin stearate, esuprone, fenofibrate, flecainide, furosemide, fluconazole, gallopamil HCl, glibenclamide, hydrochlorothiazide, ibuprofen, indometacin, itraconazole, ketoprofen, melperone, metazachlor, nalixidic acid, naftidrofuryl, nexopamil, nifedipine, nitrendipine, nitrofurantoin, oxybutynin, paracetamol, pentoxifylline, paroxetine, prazosin, propafenone HCl, pseudoephedrine HCl, ranitidine HCl, riboflavin, selegiline HCl, sulfamethazine, sulfamethoxazole, sulfathiazole, theophylline, tolbutamide, triamterene, trimethoprim, zotepine.

The results of solution experiments with two different concentrations and comparison with the corresponding melt extrudates with PVP K 30 are in the table below.

TABLE

|  | 10% by weight in DHVP | 30% by weight in DHVP | Extrudate 30% by weight in PVP |
|---|---|---|---|
| Esuprone | RT: +<br>Recryst.: − | RT: −<br>Sol. at 70° C.<br>Recryst. after 20 h | + |
| Gallopamil HCl | RT: +<br>Sol. at 60° C.<br>Recryst.: − | RT: −<br>Sol. at 60° C.<br>Recryst. after 96 h | + |
| Ibuprofen | RT: +<br>Recryst.: − | RT: +<br>Recryst.: − | + |
| Nifedipine | RT: −<br>Sol. at 50° C.<br>Recryst.: − | RT: −<br>Sol. at 50° C.<br>Recryst. after 24 h | + |
| Paracetamol | RT: −<br>Sol. at 90° C. | RT: −<br>Sol. at 90° C. | + |
| Zotepine | Recryst.: −<br>RT: +<br>Recryst.: − | Recryst.: −<br>RT: −<br>Sol. at 70° C.<br>Recryst. after 40 h | + |

RT: Room temperature
+: Solution (solid or liquid)
−: no solution

All the active ingredients listed above which form solid solutions on extrusion also dissolve in DHVP in the temperature range between room temperature and 140° C. which is typical of extrusion.

For comparison:

Theophylline insoluble in DHVP, no solid solution with PVP soluble in DMSO (dimethyl sulfoxide)

Ibuprofen soluble in DHVP, solid solution with PVP soluble in DMSO

Whereas there is a correlation between solubility and the formation of solid solutions for the DHVP test system, no such correlation exists for DMSO.

We claim:

1. A method for identifying bioactive substances which are capable of forming stable solid solutions or solid dispersions in polyvinylpyrrolidone, comprising (a) mixing one or more bioactive substances with 1,3-bis(1-pyrrolidonyl) butane to form a solution or dispersion;

(b) assessing the resulting solution or dispersion spectroscopically; and (c) selecting the bioactive substances that do not recrystallize out of the solution or dispersion.

2. A method as claimed in claim 1, wherein the solution or dispersion of the one or more bioactive substances and the 1,3-bis(1-pyrrolidonyl)butane is heated to a maximum of 140° C.

3. A method as claimed in claim 1, wherein the resulting solution or dispersion is assessed microscopically.

4. A method as claimed in claim 1, wherein, in step (a), the one or more bioactive substances and the 1,3-bis(1-pyrrolidonyl)butane are stirred, optionally with heating, and in step (c), the bioactive substances that do not recrystallize after the stirring is stopped, or after the solution or dispersion is cooled, are selected.

5. A method as claimed in claim 4, further comprising (d) investigating the selected bioactive substances for long term stability of their solution or dispersion in 1,3-bis(1-pyrrolidonyl)butane.

* * * * *